(12) United States Patent
Dijkstra et al.

(10) Patent No.: US 11,247,066 B2
(45) Date of Patent: Feb. 15, 2022

(54) IRRADIATION DEVICE

(71) Applicant: Light Tree Ventures Holding B.V., Rijswijk (NL)

(72) Inventors: Alain Dijkstra, Amstelveen (NL); Michael Kasbergen, Schoonhoven (NL)

(73) Assignee: Light Tree Ventures Holding B.V., Rijswijk (NL)

( * ) Notice: Subject to any disclaimer, the term of this patent is extended or adjusted under 35 U.S.C. 154(b) by 0 days.

(21) Appl. No.: 16/901,024

(22) Filed: Jun. 15, 2020

(65) Prior Publication Data

US 2021/0387014 A1    Dec. 16, 2021

(51) Int. Cl.
*A61N 5/06* (2006.01)

(52) U.S. Cl.
CPC .... *A61N 5/0613* (2013.01); *A61N 2005/0632* (2013.01); *A61N 2005/0652* (2013.01); *A61N 2005/0653* (2013.01); *A61N 2005/0659* (2013.01); *A61N 2005/0661* (2013.01); *A61N 2005/0662* (2013.01)

(58) Field of Classification Search
None
See application file for complete search history.

(56) References Cited

U.S. PATENT DOCUMENTS

| 4,905,690 | A | * | 3/1990 | Ohshiro | A61N 5/0616 607/89 |
|---|---|---|---|---|---|
| 7,083,299 | B2 | | 8/2006 | Chapman | |
| 8,415,879 | B2 | | 4/2013 | Lowenthal et al. | |
| 8,809,126 | B2 | | 8/2014 | Lowenthal et al. | |
| 8,846,457 | B2 | | 9/2014 | Lowenthal et al. | |
| 8,852,467 | B2 | | 10/2014 | Lowenthal et al. | |
| 8,877,101 | B2 | | 11/2014 | Lowenthal et al. | |
| 9,018,833 | B2 | | 4/2015 | Lowenthal et al. | |
| 10,569,101 | B2 | * | 2/2020 | Wu | A61N 5/06 |
| 10,588,632 | B2 | * | 3/2020 | Shelton, IV | A61B 17/0682 |

(Continued)

FOREIGN PATENT DOCUMENTS

| CN | 202791418 U | 3/2013 |
|---|---|---|
| CN | 204805995 U | 11/2015 |
| CN | 207065451 U | 3/2018 |

*Primary Examiner* — Nathan J Jenness
*Assistant Examiner* — Skylar Lindsey Christianson
(74) *Attorney, Agent, or Firm* — Emanus, LLC; Willie Jacques

(57) ABSTRACT

An irradiation device capable of emitting electromagnetic radiation at variable beam angles, comprises a housing assembly including a longitudinal shell, the longitudinal shell having a first end and a second end, a first end cap assembly provided at the first end of the longitudinal shell, and a second end cap assembly provided at the second end of the longitudinal shell, a radiation source provided within the longitudinal shell, a movable lens having two ends, a first end of the movable lens provided within the first end cap assembly and a second end of the movable lens provided within the second end cap assembly, and one or more translational mechanisms provided within one or more of the first end cap assembly and the second end cap assembly, wherein the one or more translational mechanisms are adapted to cause linear motion of the movable lens with respect to the radiation source.

11 Claims, 14 Drawing Sheets

(56) References Cited

U.S. PATENT DOCUMENTS

| | | | |
|---|---|---|---|
| 2002/0161418 A1* | 10/2002 | Wilkens | H01J 61/125 |
| | | | 607/90 |
| 2010/0036245 A1* | 2/2010 | Yu | A61N 5/1027 |
| | | | 600/439 |
| 2012/0212953 A1* | 8/2012 | Bloom | H05B 45/52 |
| | | | 362/223 |
| 2016/0129279 A1* | 5/2016 | Ferolito | A61N 5/0618 |
| | | | 607/89 |
| 2016/0367833 A1* | 12/2016 | Salinas | A61N 5/0616 |
| 2020/0315907 A1* | 10/2020 | Dijkstra | A61H 1/00 |

* cited by examiner

IRRADIATION DEVICE

TECHNICAL FIELD

The present invention generally relates to irradiation devices. More specifically, the present invention relates to irradiation devices that are capable of emitting electromagnetic radiations at variable beam angles.

BACKGROUND ART

Irradiation devices have been known in the art for some time now and are being used in several applications such as medical imaging, therapeutic and recreational applications for pain relief and skincare and spatial lighting applications, etc. However, conventionally available irradiation devices have been known to be designed to emit electromagnetic radiations at a given preconfigured beam angle.

A beam angle, by generally accepted definition in the art, is an angle subtended by two points where the intensity of the emitted radiation is fifty percent of the intensity at a center of a beam spread of a radiation beam. However, with the advancement of technology, devices have been introduced that allow different beam angles to be achieved from within a single device. However, such devices are limited to alternating between a small number of preconfigured discreet beam angles, are generally bulky in construction, and are severely cost-intensive.

Therefore, there is a need in the art for an irradiation device that does not suffer from the aforementioned deficiencies.

OBJECTS OF THE INVENTION

Some of the objects of the present invention are listed below:

It is an object of the present invention to provide an irradiation device that emits electromagnetic radiations at variable beam angles;

It is an additional object of the present invention to provide an irradiation device which is beneficial for both personal and commercial use;

It is an additional object of the present invention to provide an irradiation device which is simple in construction, configuration and operation;

It is an additional object of the present invention to provide an irradiation device that offers an economical way to obtain variable beam angles from within a single irradiation device; and It is a furthermore object of the present invention to provide an irradiation device that is convenient to use.

Other objects, features, advantages, and goals of the present invention will be better understood from the following detailed description taken in conjunction with the accompanying drawings.

SUMMARY

According to a first aspect of the present invention, there is provided an irradiation device capable of emitting electromagnetic radiation at variable beam angles, the irradiation device comprising a housing assembly including a longitudinal shell, the longitudinal shell having a first end and a second end, a first end cap assembly provided at the first end of the longitudinal shell, a second end cap assembly provided at the second end of the longitudinal shell, and one or more locking arrangements provided at one or more of the first and the second ends of the longitudinal shell, the one or more locking arrangements being adapted to prevent linear motion and/or accidental rotational motion of the one or more of first and the second end cap assemblies with respect to the one or more of first and the second ends of the longitudinal shell, respectively. The irradiation device further includes a radiation source provided within the longitudinal shell, wherein the radiation source is configured to emit electromagnetic radiation, and the longitudinal shell is made from a material that is at least partially transparent to the electromagnetic radiation emitted by the radiation source, a movable lens having two ends, a first end of the movable lens provided within the first end cap assembly and a second end of the movable lens provided within the second end cap assembly, wherein the movable lens is located between the radiation source and the longitudinal shell and one or more translational mechanisms provided within one or more of the first end cap assembly and the second end cap assembly, wherein the one or more translational mechanisms are adapted to cause linear motion of the movable lens with respect to the radiation source.

In one embodiment of the invention, at least a segment of the longitudinal shell has been embodied as a fixed lens.

In one embodiment of the invention, the irradiation device further comprises a fixed lens in the form of a discrete member located between the radiation source and the longitudinal shell.

In one embodiment of the invention, the radiation source is configured to be deactivated during the linear motion of the movable lens.

In one embodiment of the invention, the one or more of the first and the second end cap assemblies are adapted to be rotated manually with respect to the longitudinal shell, thereby causing the actuation of the respective one or more translational mechanisms.

In one embodiment of the invention, each one of the one or more locking arrangements includes a locking body mounted on a locking spring, the locking body being adapted to engage with shape compliant grooves provided within the first and the second end cap assemblies.

In one embodiment of the invention, one or more electrical motors provided within one or both of the first end cap assembly and the second end cap assembly, wherein the one or more electrical motors are configured to cause the actuation of the respective one or more translational mechanisms.

In one embodiment of the invention, each one of the one or more locking arrangements is constituted by one or more self-locking shafts provided with the one or more respective electrical motors.

In one embodiment of the invention, each one of the one or more the translational mechanisms is constituted by a cam that is adapted to rotate on the actuation of the respective translational mechanism and a cam follower provided at an end of the movable lens.

In one embodiment of the invention, the radiation source is configured to emit electromagnetic radiation in Ultra-Violet (UV), visible light, and Infrared (IR) wavelengths bands of the electromagnetic spectrum.

In one embodiment of the invention, the radiation source is configured to emit electromagnetic radiation in any one of a pulse mode and continuous mode.

In one embodiment of the invention, the radiation source includes one or more Light Emitting Diodes (LEDs).

In one embodiment of the invention, the one or more LEDs have been provided on an Organic LED (OLED) based flexible panel or an inorganic LED based flexible panel.

In one embodiment of the invention, the one or more LEDs are provided as a printable composition of micro-LEDs, printed on a substrate.

According to a second aspect of the present invention, there is provided a method of utilizing an irradiation device capable of emitting electromagnetic radiation at variable beam angles, the irradiation device comprising a housing assembly including a longitudinal shell, the longitudinal shell having a first end and a second end, a first end cap assembly provided at the first end of the longitudinal shell, and a second end cap assembly provided at the second end of the longitudinal shell, a radiation source provided within the longitudinal shell, wherein the radiation source is configured to emit electromagnetic radiation, and the longitudinal shell is made from a material that is at least partially transparent to the electromagnetic radiation emitted by the radiation source, a movable lens having two ends, a first end of the movable lens provided within the first end cap assembly and a second end of the movable lens provided within the second end cap assembly, wherein the movable lens is located between the radiation source and the longitudinal shell and one or more translational mechanisms provided within one or more of the first end cap assembly and the second end cap assembly, wherein the one or more translational mechanisms are adapted to cause linear motion of the movable lens with respect to the radiation source. The method comprising a step of actuating the one or more translational mechanisms to cause linear motion of the movable lens.

In the context of the specification, the term "diaphanous materials" refers to the materials that allow the transmission of electromagnetic radiation, including at least Ultra-Violet (UV), visible light, and Infrared (IR), through them.

In the context of the specification, the term "linear motion" refers to the one-dimensional motion along a straight line.

In the context of the specification, the term "luminescent materials" refers to the materials that emit radiation (IR to UV frequency band, inclusive of IR and UV frequencies) under external energy excitation. The energy applied, in the form of high energy electron, photons, or electric field, can then be re-emitted in the form of electromagnetic radiation.

In the context of the specification, the term "refractive index" of a material refers to the ratio of the speed of radiation (such as light) in a medium formed from such material to the speed of radiation in a pure vacuum.

The following detailed description is illustrative and is not intended to be in any way limiting. In addition to the illustrative aspects, embodiments, and features described above, further aspects, embodiments, and features will be apparent by reference to the following detailed description in conjunction with the accompanying drawings.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

Figure 1A:
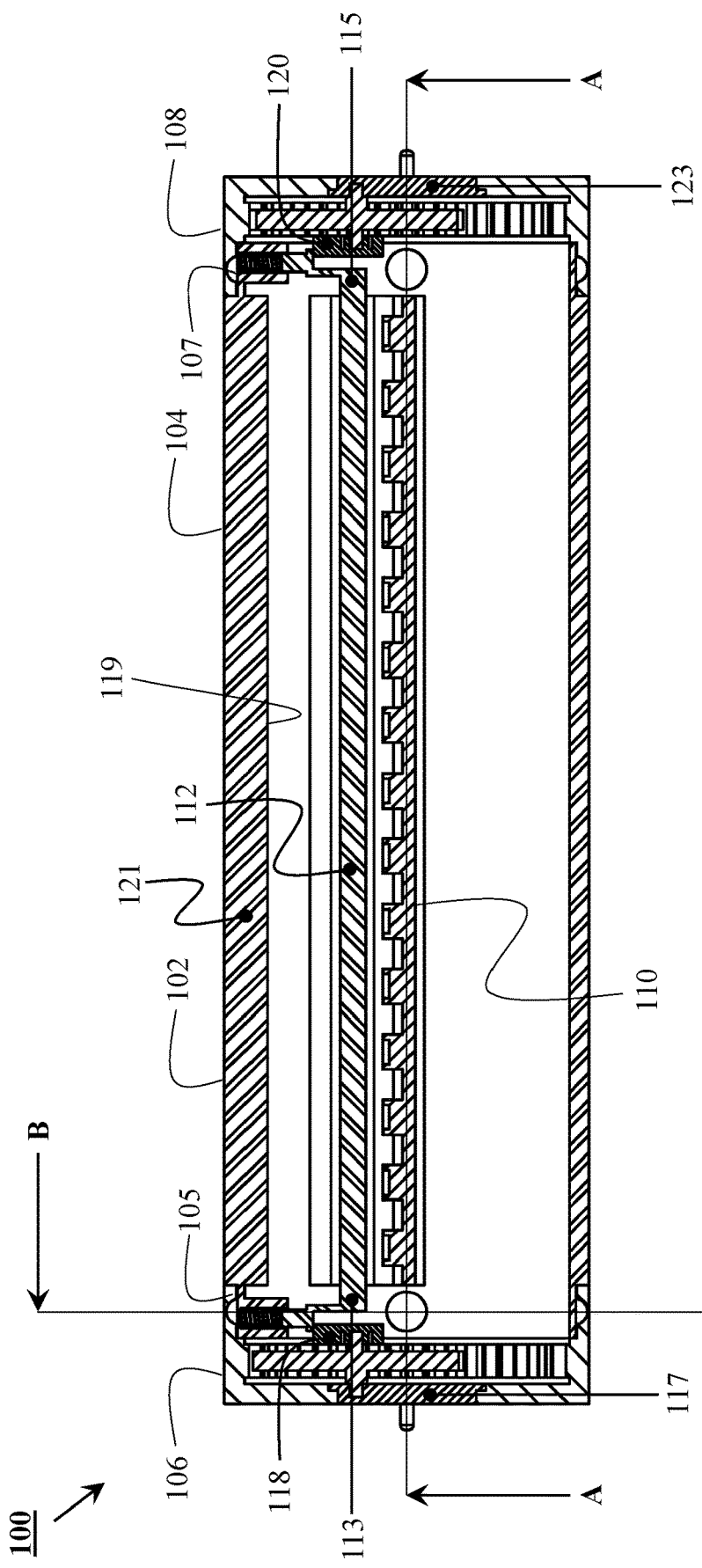
FIG. 1A illustrates a front sectional view of an irradiation device, in accordance with an embodiment of the present invention.

While the present invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims and equivalents thereof.

DETAILED DESCRIPTION

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

The present invention provides an irradiation device that is capable of emitting electromagnetic radiation at variable beam angles. It is to be noted here that in the context of this specification, terms like "light", "radiation", "irradiation", "emission" and "illumination", etc. refer to electromagnetic radiation in frequency ranges varying from the Ultraviolet (UV) frequencies to Infrared (IR) frequencies and wavelengths, wherein the range is inclusive of UV and IR frequencies and wavelengths. It is to be further noted here that UV radiation can be categorized in several manners depending on respective wavelength ranges, all of which are envisaged to be under the scope of this invention. For example, UV radiation can be categorized as, Hydrogen Lyman-α (122-121 nm), Far UV (200-122 nm), Middle UV (300-200 nm), Near UV (400-300 nm). The UV radiation may also be categorized as UVA (400-315 nm), UVB (315-280 nm), and UVC (280-100 nm). Similarly, IR radiation may also be categorized into several categories according to respective wavelength ranges which are again envisaged to be within the scope of this invention. A commonly used subdivision scheme for IR radiation includes Near IR (0.75-1.4 μm), Short-Wavelength IR (1.4-3 μm), Mid-Wavelength IR (3-8 μm), Long-Wavelength IR (8-15 μm) and Far IR (15-1000 μm).

The irradiation device of the present invention has been envisaged to be embodied in a form factor of a linear Light Emitting Diode (LED) tube so that it can easily be mounted on readily available electrical fixtures and hence the invention does not necessitate any significant structural redesign of the fixtures and provide savings on capital investment. In that regard, variations in the beam angle have been achieved through relative linear motion between a fixed lens and a movable lens provided in a longitudinal shell of the irradiation device. The fixed lens and the movable lenses may have identical, similar, or dissimilar optical characteristics, such as thickness, focal length, concavity, refractive index, color coating, and polarization, etc., depending upon specific applications of the irradiation device.

It is further envisaged, although not bindingly, that the radiation source may include Light Emitting Diodes (LEDs) for the invention, because LEDs are relatively more power-efficient than other devices and technologies used for generating electromagnetic radiation, such as fluorescent, halogen, and incandescent lamps. The LEDs in that regard may be mounted on a Printed Circuit Board (PCB) through Surface Mounting Technology (SMT). SMT permits the creation of smaller PCB designs by allowing components to be placed closer together on the board that makes the device more lightweight and compact. The SMT process is faster to set up for production and requires less manufacturing cost than its counterpart, through-hole technology because it does not require the circuit board to be drilled for assembly.

In spatial lighting applications, the irradiation device may be designed to get the desired beam angle of the illumination provided by the irradiation device. The irradiation device in that regard is envisaged to emit visible light at well-known ranges of beam angles including spot (4-19 degrees), flood (20-35 degrees), wide flood (36-49 degrees), and very wide flood (50-120 degrees or more). However, the invention is not limited to the aforementioned beam angle ranges alone. Referring to the figures, the invention will now be described in further detail.

FIG. 1A illustrates a front sectional view of an irradiation device 100, in accordance with an embodiment of the present invention. The irradiation device 100 as illustrated in FIG. 1A has been embodied in the form of an LED linear tube so that it can easily be installed in fixtures already available for the fluorescent tubes available in the market. This would allow the irradiation device 100 to be adopted with relative convenience without causing any infrastructural expenditures. However, in several alternative embodiments, the irradiation device 100 may be constructed in several alternative shapes and sizes depending upon their specific applications. The irradiation device 100 as shown in FIG. 1A includes a housing assembly 102 which serves to encapsulate other elements and components of the irradiation device 100. The housing assembly 102 includes a longitudinal shell 104 that can be made from a material having good diaphanous properties. For example, the longitudinal shell 104 can be made from glass, plastic, acrylic, or any other diaphanous material which are transparent or translucent to the electromagnetic radiations that would be required for a given application.

In several embodiments, phosphor coatings may also be provided for example on an inner surface 119 of the longitudinal shell 104 to achieve the illumination in colors required by specific applications. For example, Yttrium Aluminum Garnet (YAG) can be used in combination with a blue LED to generate white light and Magnesium doped potassium fluorosilicate can be used in combination with blue LED to generate red light. Additionally, near Ultra Violet (UV) LEDs may be combined with europium based phosphors to generate red and blue lights and copper and zinc doped zinc sulfide-based phosphors to generate green light. The longitudinal shell 104 can also be made of any one or combinations of nano plastic materials being used in the field of LED linear tubes.

For clarity, it is to be noted that the nano plastic materials being used in the field of LED linear tubes generally, or the longitudinal shell 104 in particular, differ from micro and nano plastic particles (also sometimes referred to as secondary nano plastic materials) generated due to degradation of used plastic products. The nano plastic materials (also sometimes referred to as primary nano plastic materials) used in the field of LED linear tubes offer improved mechanical properties like hardness, stiffness, etc. over the over existing available material used in tube light manufacturing. One of the several advantages of using the nano plastic materials is that the nano plastic materials make the irradiation device 100 highly resilient to damage, even when compared to the already robust polycarbonate and aluminum materials used in most LED linear tubes in the art.

The longitudinal shell 104 has a first end 105 and a second end 107. Further, a first end cap assembly 106 has been provided at the first end 105 of the longitudinal shell 104, and a second end cap assembly 108 has been provided at the second end 107 of the longitudinal shell 104. It is envisaged that in several embodiments, external diameters of the first end 105 and the second end 107 be smaller than the external diameter of the longitudinal shell 104, forming two step-like extensions at the ends of the longitudinal shell 104 that may be inserted into the first 106 and the second 108 end cap assemblies to ensure that the first 106 and the second 108 end cap assemblies are flush with the longitudinal shell 104.

A radiation source 110 capable of emitting electromagnetic radiations has been provided within the longitudinal shell 104. The radiation source 110 may be configured to emit electromagnetic radiation in Ultra-Violet (UV), visible light, and Infrared (IR) wavelengths bands of the electromagnetic spectrum, depending upon specific application of the irradiation device 100. Further, the longitudinal shell 104 is made from a material that is at least partially transparent to the electromagnetic radiation emitted by the radiation source 110. In several embodiments of the invention, the radiation source 110 may include a plurality of Light Emitting Diodes (LEDs). The LEDs are characterized by their superior power efficiencies, smaller sizes, rapidity in switching, physical robustness, and longevity when compared with incandescent or fluorescent lamps. In that regard, the one or more LEDs may be through-hole type LEDs (generally used to produce electromagnetic radiations of red, green, yellow, blue and white colors), Surface Mount LEDs, Bi-color LEDs, Pulse Width Modulated RGB (Red-Green-Blue) LEDs, and high power LEDs, etc.

Materials used in the one or more LEDs may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultra Violet (UV) LEDs may be combined with europium based phosphors to generate red and blue lights and copper and zinc doped zinc sulfide-based phosphor to generate green light.

In addition to conventional mineral-based LEDs, one or more LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in Bardsley, J. N (2004), *"International OLED Technology Roadmap"*, *IEEE Journal of Selected Topics in Quantum Electronics, Vol. 10, No. 1*, that is included herein in its entirety, by reference. An exemplary description of flexible inorganic light-emitting diode strips can be found in granted U.S. Pat. No. 7,476,557B2, titled "Roll-to-roll fabricated light sheet and encapsulated semiconductor circuit devices", which is included herein in its entirety, by reference.

In several embodiments, the one or more LEDs may also be micro-LEDs described through U.S. Pat. Nos. 8,809,126B2, 8,846,457B2, 8,852,467B2, 8,415,879B2, 8,877,101B2, 9,018,833B2, and their respective family members, assigned to Nth Degree Technologies Worldwide Inc., which are included herein by reference, in their entirety. The one or more LEDs, in that regard, may be provided as a printable composition of the micro-LEDs, printed on a substrate.

The irradiation device 100 further includes a movable lens 112 having two ends. A first end 113 of the movable lens 112 has been provided within the first end cap assembly 106, and a second end 115 of the movable lens 112 has been provided within the second end cap assembly 108. Also, the movable lens 112 has been located between the radiation source 110 and the longitudinal shell 104. Also, one or more translational mechanisms in forms of a first translational mechanism 118 and a second translational mechanism 120, have been provided within the first end cap assembly 106 and the second end cap assembly 108, respectively. The first 118 and the second 120 translational mechanisms are adapted to cause linear motion of the movable lens 112, with respect to the radiation source 110. Also, wherein at least a segment 121 of the longitudinal shell 104 has been embodied as a fixed lens.

Figure 1B:
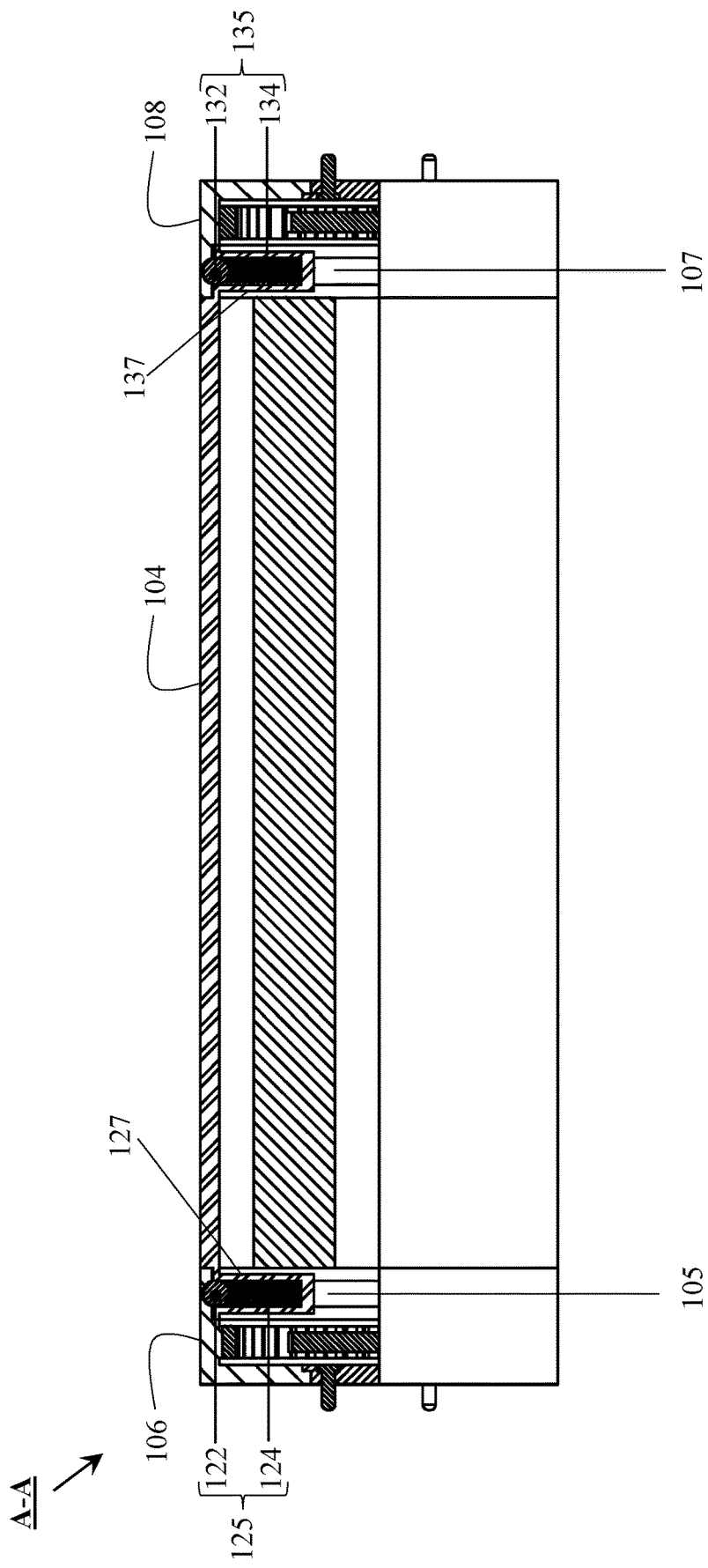
FIG. 1B illustrates a partial sectional view along a plane A-A of the irradiation device of FIG. 1A.

FIG. 1B illustrates a partial sectional view along a plane A-A of the irradiation device 100 of FIG. 1A. As illustrated in FIG. 1B, a first locking arrangement 125 has been provided at the first end 105 of the longitudinal shell 104 and a second locking arrangement 135 at the second end 107 of the longitudinal shell 104. The first locking arrangement 125 includes a first locking body 122 that is mounted on a first locking spring 124 provided within a first groove element 127 attached with the first end 105. The first locking body 122 may be in the form of a sphere and be adapted to engage with a shape compliant groove provided within the first end cap assembly 106. In that manner, once the first end cap assembly 106 has been installed at the first end 105 of the longitudinal shell 104, the force generated by the first locking spring 124 of the first locking arrangement 125 would be able to prevent any linear motion and/or accidental rotational motion of the first end cap assembly 106 with respect to the longitudinal shell 104.

Similarly, the second locking arrangement 135 includes a second locking body 132 that is mounted on a second locking spring 134 provided within a second groove element 137 attached with the second end 107. The second locking body 132 may also be in the form of a sphere and be adapted to engage with a shape compliant groove provided within the second end cap assembly 108. In that manner, once the second end cap assembly 108 has been installed at the second end 107 of the longitudinal shell 104, the force generated by the second locking spring 134 of the second locking arrangement 135 would be able to prevent any linear motion and/or accidental rotational motions of the second end cap assembly 108 with respect to the longitudinal shell 104.

Figure 1C:
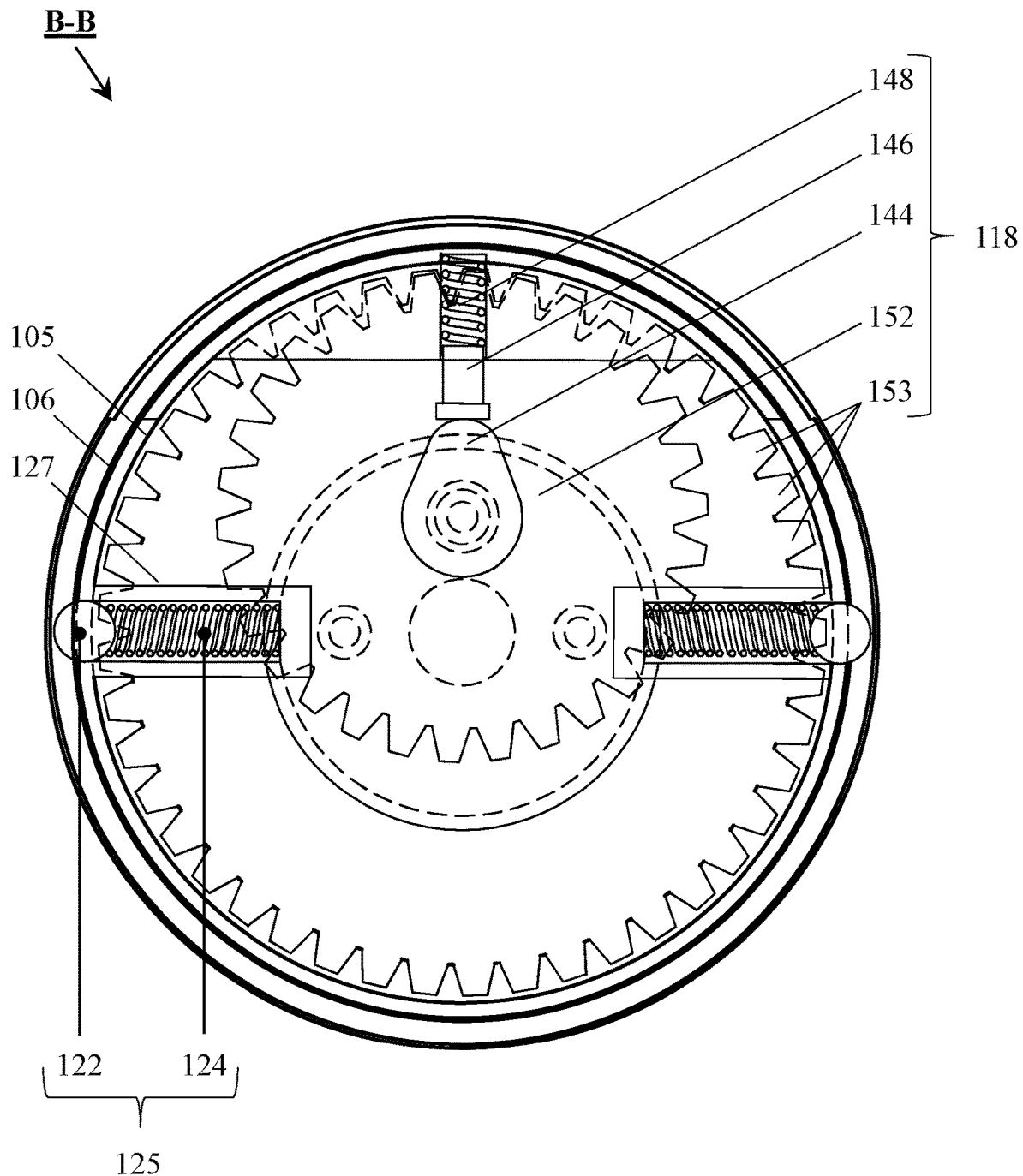
FIG. 1C illustrates a sectional view along a plane B-B of the irradiation device of FIG. 1C.

FIG. 1C illustrates a sectional view along a plane B-B of the irradiation device of FIG. 1C. As illustrated in FIG. 1C, the first translational mechanism 118 has been provided within the first end cap assembly 106. The first translational mechanism 118 is constituted by a first cam 144 that is coupled with a first gear element 152 and a first cam follower 146 provided at the first end 113 of the movable lens 112. An inner surface of the first end cap assembly 106 has been provided with a first set of internal gear teeth 153 that are adapted to mesh with the first gear element 152. Further, the first cam follower 146 is attached to a first biasing spring element 148 that has also been provided at the first end 113 of the movable lens 112. The first biasing spring element 148 keeps the first cam follower 146 always in contact with the first cam 144. The manual rotation of the first end cap assembly 106 actuates the first translational mechanism 150 that causes the rotation of the first cam 144, thereby causing the linear motion of the movable lens 112 with respect to the radiation source 110.

Figure 1D:
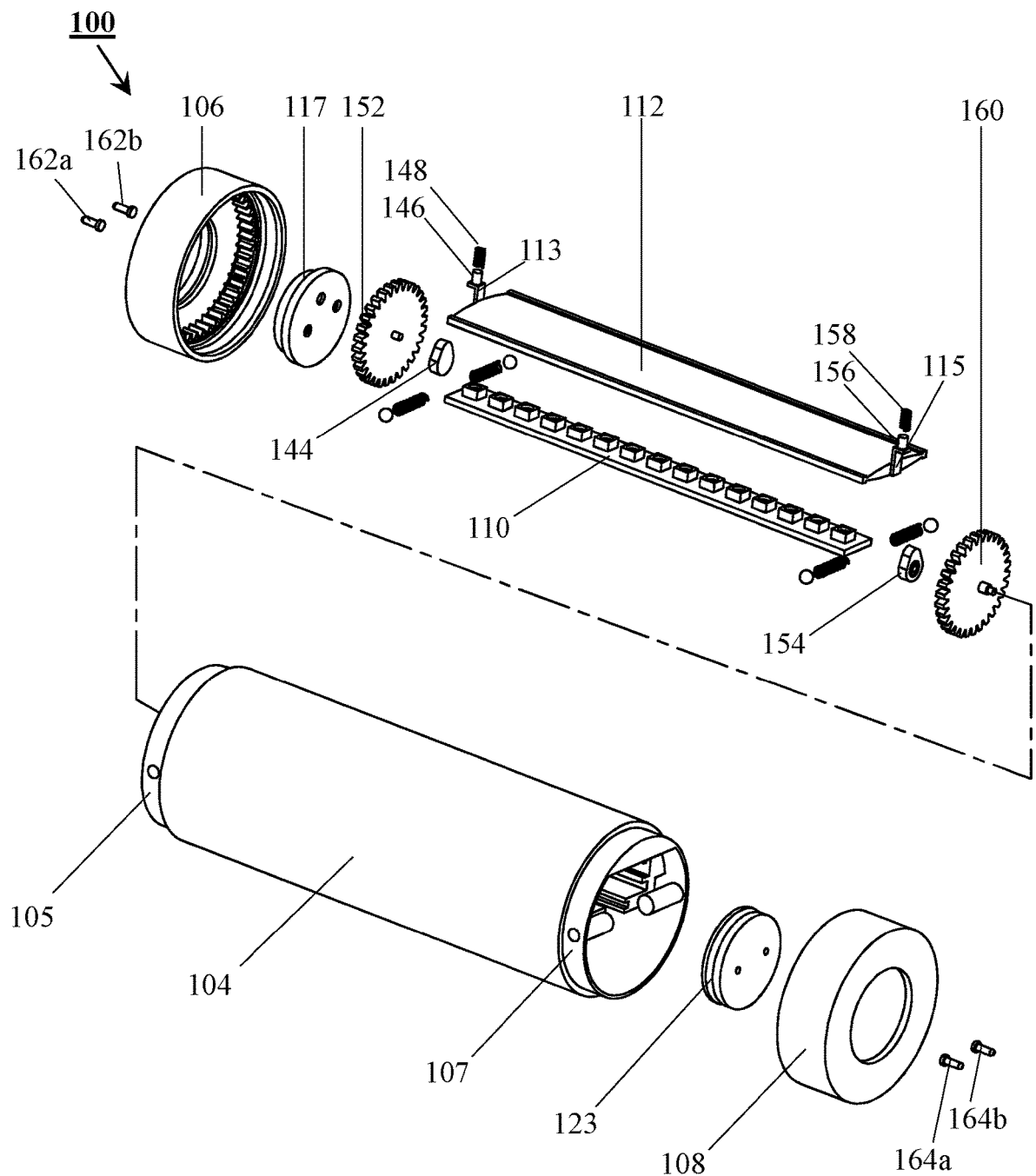
FIG. 1D illustrates an exploded view of the irradiation device of FIG. 1A.

FIG. 1D illustrates an exploded view of the irradiation device 100 of FIG. 1A. In addition to the elements of the irradiation device 100 as discussed above, FIG. 1D further illustrates a second cam follower 156 and a second biasing spring element 158 provided at the second end 115 of the movable lens 112. A second cam 154 coupled with a second gear element 160, and the second cam follower 156 provided at the second end 115 of the movable lens 112 constitute the second translational mechanism 120, provided within the second end cap assembly 108. The second end cap assembly 108 may also be provided with a second set of internal teeth capable of meshing with the second gear element 160. In that manner, the first 106 and the second 108 end cap assemblies may be rotated individually for adjustment of the movable lens 112.

It is further a design objective that the first 106 and the second 108 end cap assemblies be rotatable even when the irradiation device 100 has been installed in a fixture. In order to ensure unobstructed rotation of the first 106 and the second 108 end cap assemblies, first electrical terminals 162 (162a, 162b) have been provided on a first discrete disc 117 and second electrical terminals 164 (164a, 164b) have been provided on a second discrete disc 123. The first 117 and the second 123 discrete discs, even though coaxial with the first 106 and the second 108 end cap assemblies, respectively, remain fixed between the fixtures and the first 152 and the second 160 gear elements, respectively, without rotating. This type of constructions is typically suited for bi-pin types of socket designs (shunted or non-shunted). However, a person skilled in the art would appreciate that the same concept can be extended to other kinds of socket designs, such as single pin, quad pin, or recessed double contacts, etc.

Figure 2A:
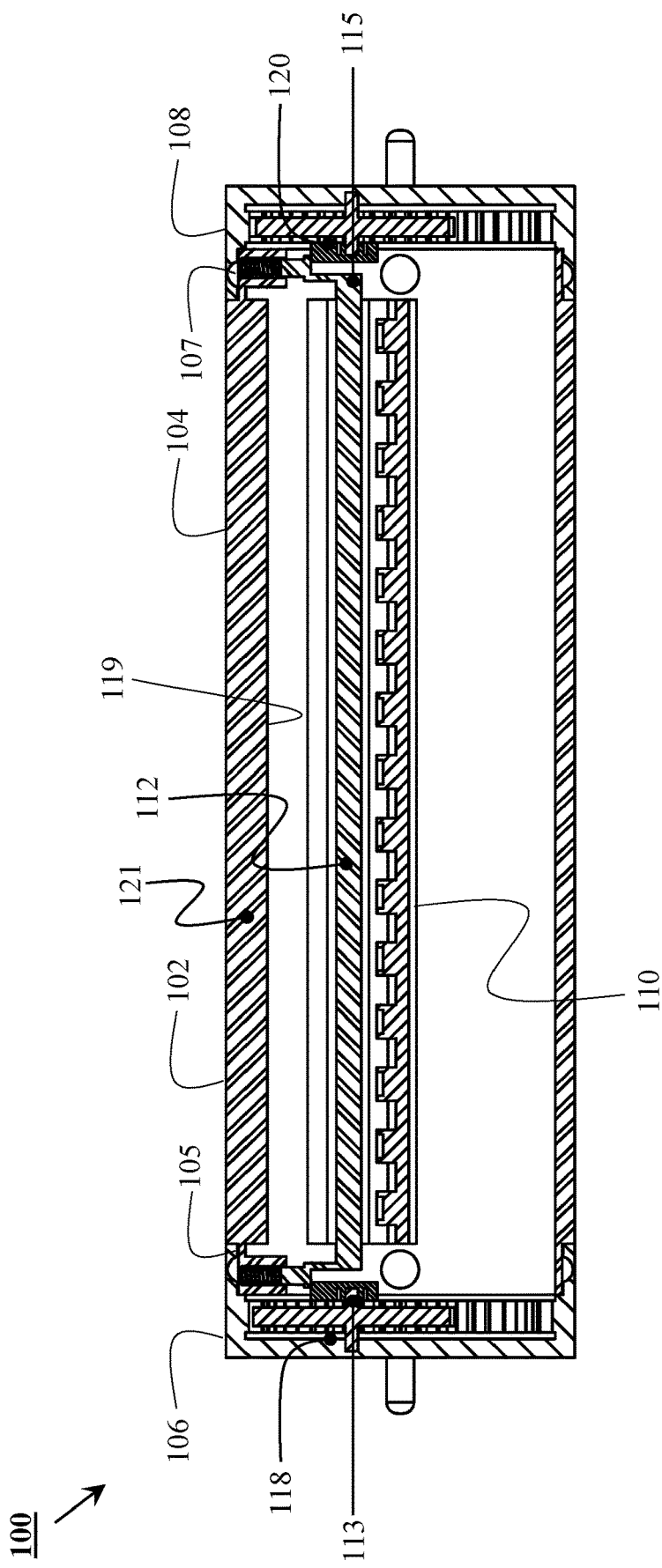
FIG. 2A illustrates a front sectional view of the irradiation device, in accordance with another embodiment of the present invention.
Figure 2B:
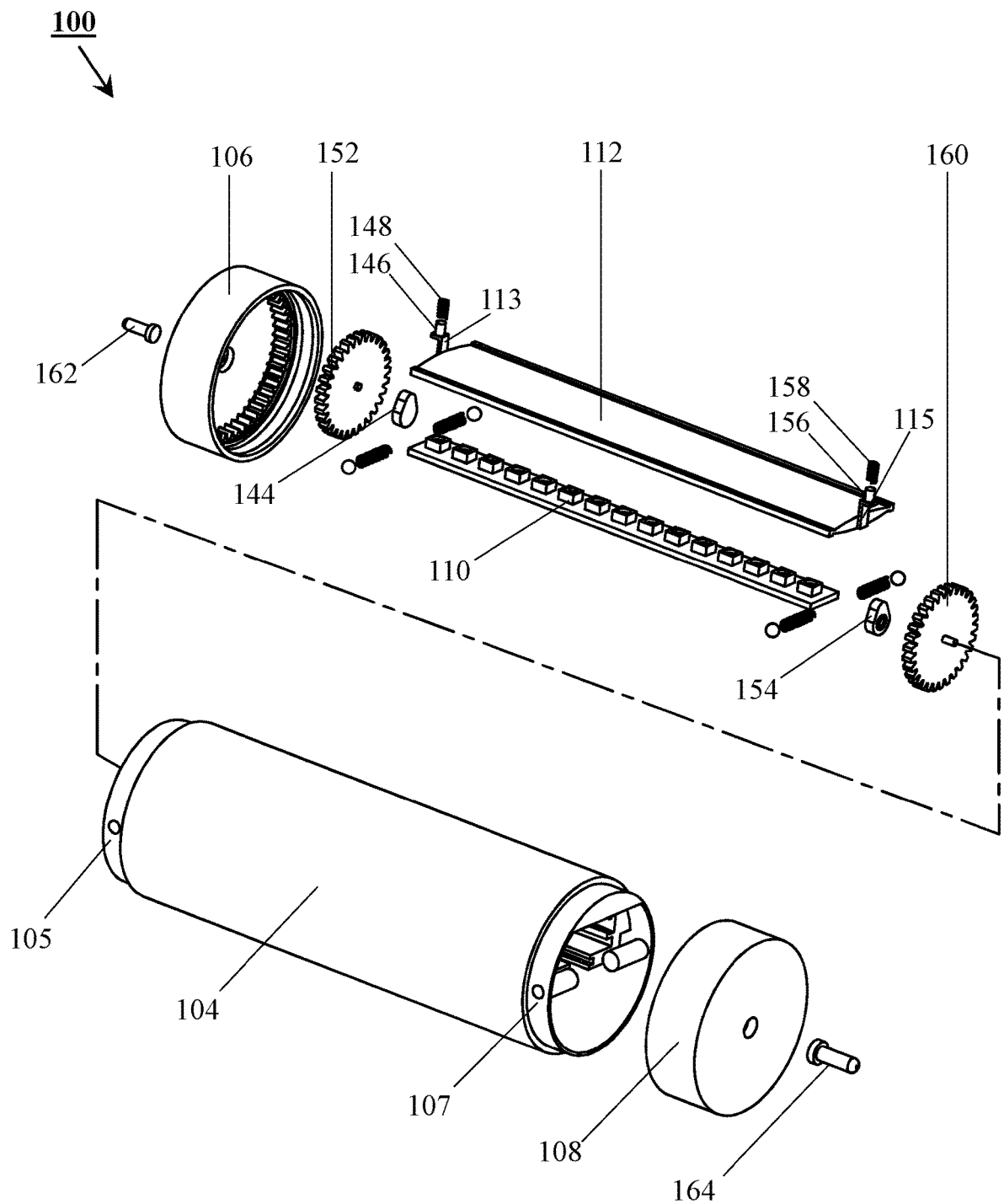
FIG. 2B illustrates an exploded view of the irradiation device of FIG. 2A.

FIG. 2A illustrates a front sectional view of the irradiation device 100, in accordance with another embodiment of the present invention. FIG. 2B illustrates an exploded view of the irradiation device 100 of FIG. 2A. It is illustrated through FIGS. 2A and 2B that the irradiation device 100 has been designed for single-pin sockets, and the first 162 and the second 164 electrical terminals may or may not be fastened to the first 106 and the second 108 end cap assemblies, respectively. In that manner, the first 162 and the second 164 electrical terminals may or may not be able to rotate within their respective sockets during rotation of the first 106 and the second 108 end cap assemblies, respectively.

Figure 3A:
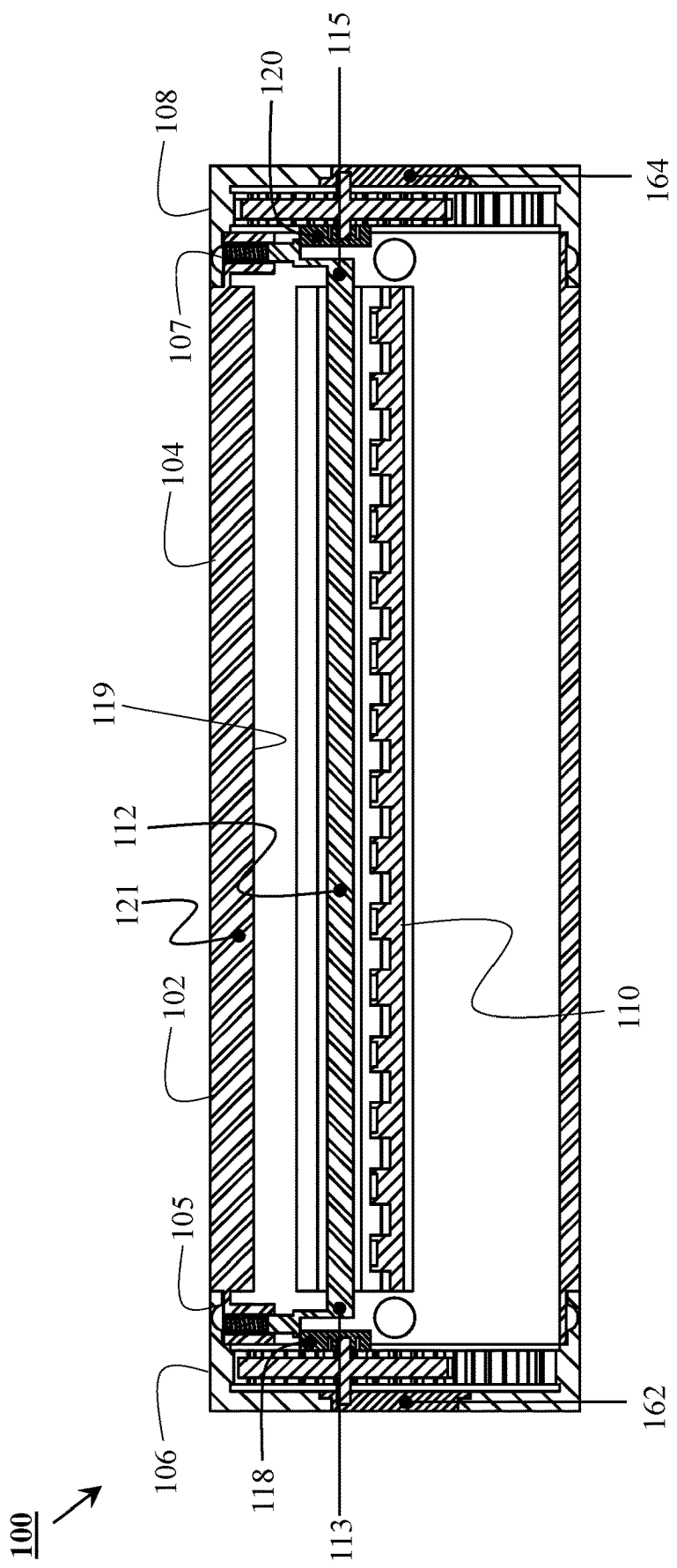
FIG. 3A illustrates a front sectional view of the irradiation device, in accordance with yet another embodiment of the present invention.

FIG. 3A illustrates a front sectional view of the irradiation device 100, in accordance with yet another embodiment of the present invention. FIG. 3A illustrates the first 162 and the second 164 electrical terminals in the form of magnetic discs that may be attached with a corresponding fixture through magnetic attraction. In this scenario as well, the first 162 and the second 164 electrical terminals remain fixedly attached with their respective electrical contacts in the fixture, while the first 106 and the second 108 end cap assemblies rotate freely with respect to the first 162 and the second 164 electrical terminals.

Figure 3B:
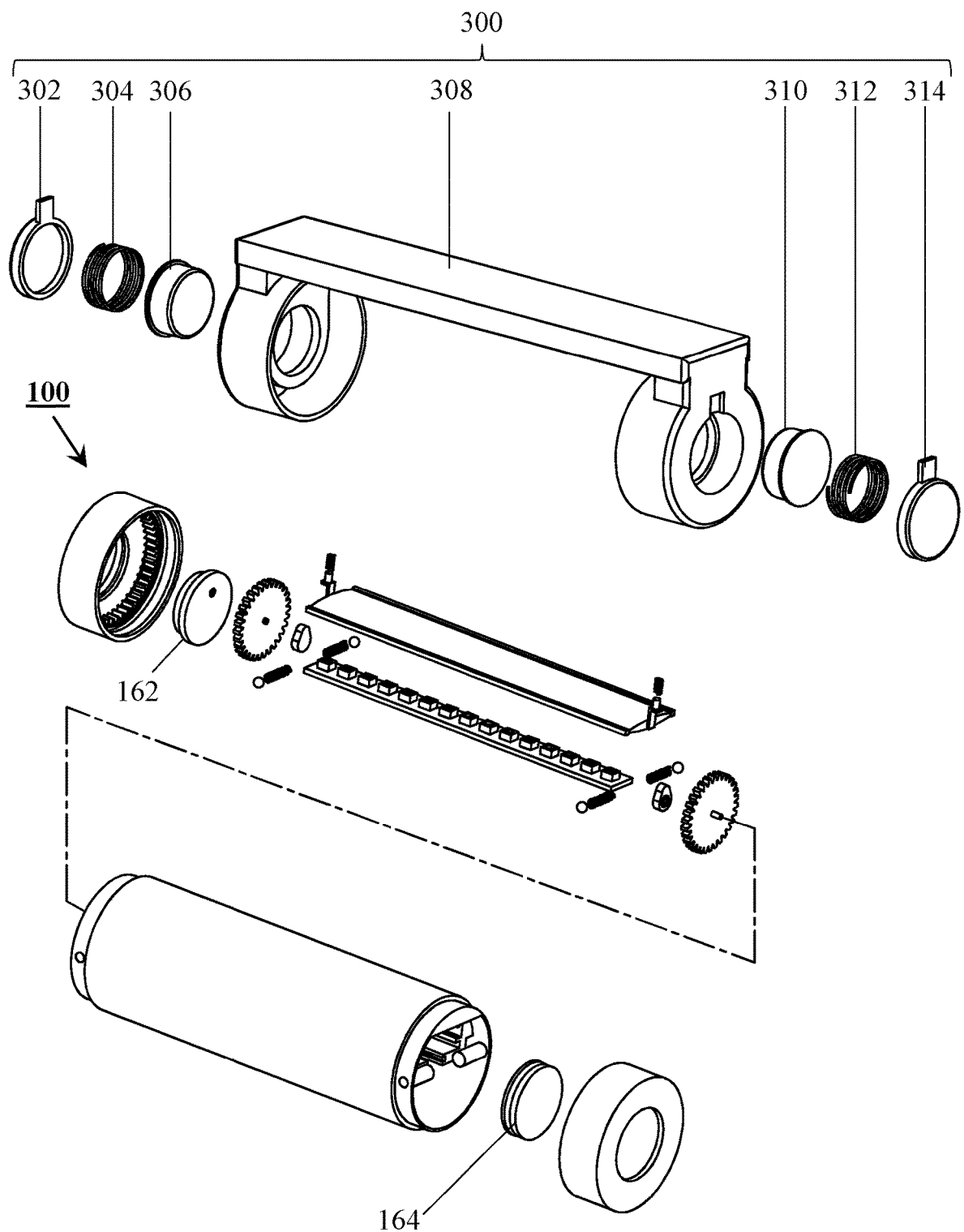
FIG. 3B illustrates an exploded view of the irradiation device of FIG. 3A.

FIG. 3B illustrates an exploded view of the irradiation device 100 of FIG. 3A. FIG. 3B illustrates a magnetic fixture 300 for the irradiation device 100 of FIG. 3A. The magnetic fixture 300 includes, inter alia, a first contact cap 302, a first contact biasing spring 304, a first electrical contact 306, a longitudinal fixture body 308, a second electrical contact 310, a second contact biasing spring 312, and a second contact cap 314. While the first 302 and the second 314 contact caps are provided as closures at the ends of the magnetic fixture 300, the first 306 and the second 310 electrical contacts are configured to supply electrical power to the irradiation device 100, by magnetically attaching with the first 162 and the second 164 electrical terminals, respectively. The magnetic attachment between the first 306 and the second 310 electrical contacts, and the first 162 and the second 164 electrical terminals, respectively, also allow the first 106 and the second 108 end cap assemblies to rotate freely with respect to the first 162 and the second 164 electrical terminals, respectively.

Figure 4A:
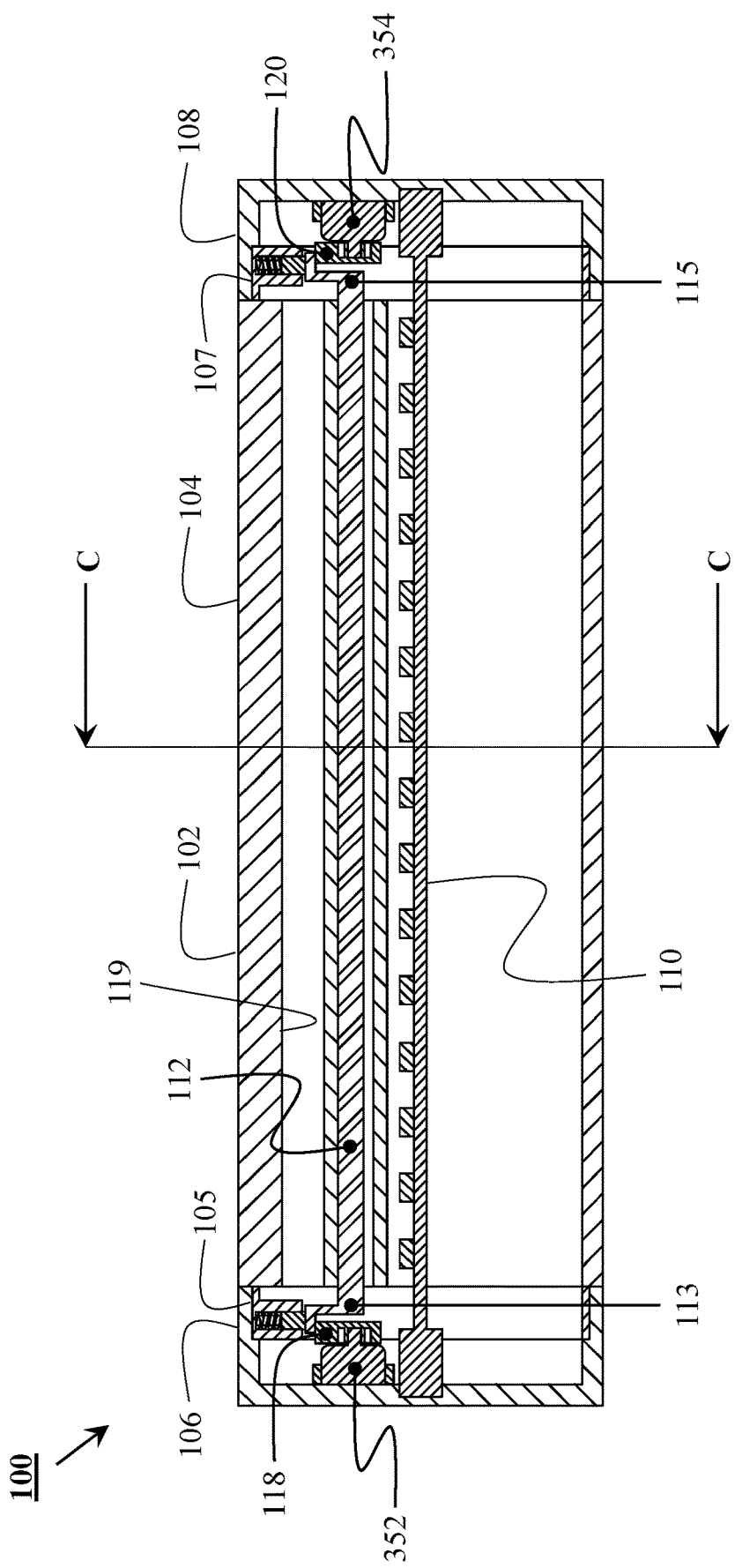
FIG. 4A illustrates a front sectional view of an irradiation device, in accordance with yet another embodiment of the present invention.
Figure 4B:
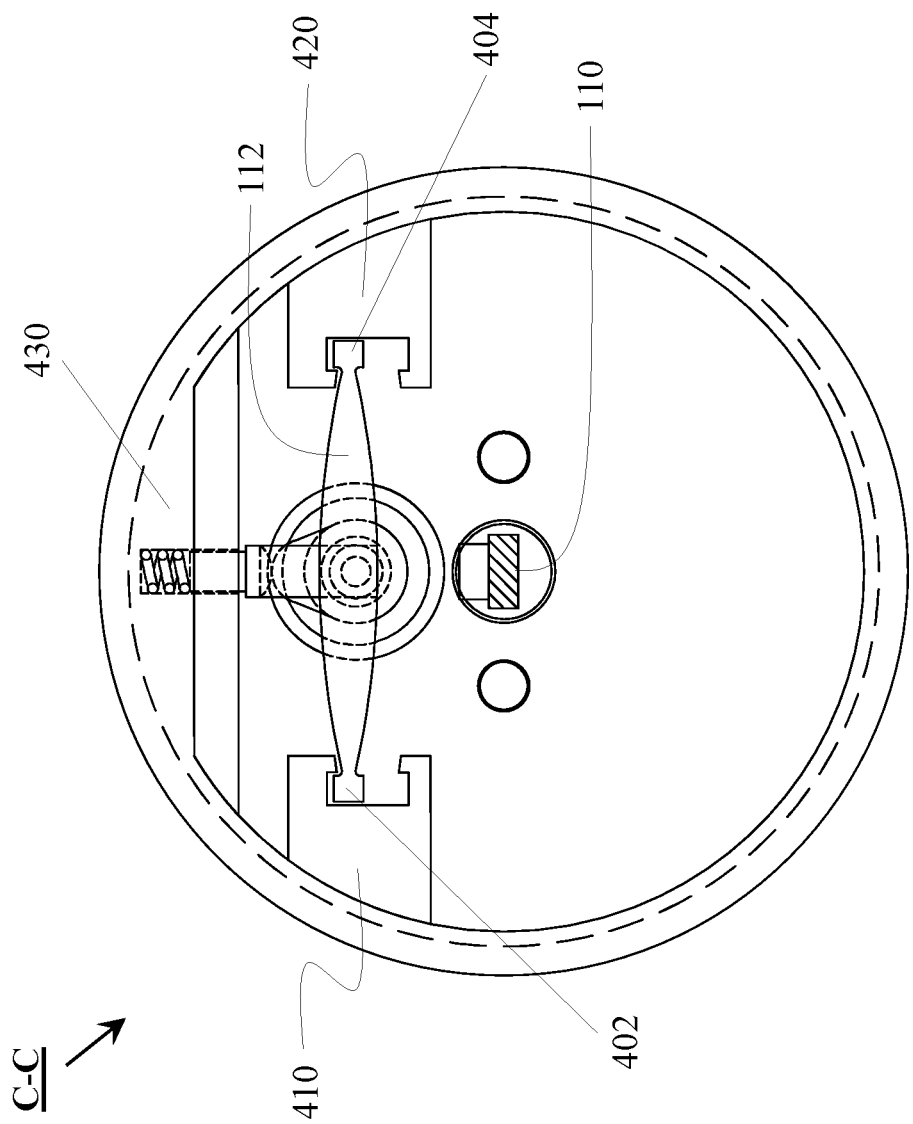
FIG. 4B illustrates a cross-sectional view of the irradiation device of FIG. 4A, along a plane C-C.

FIG. 4A illustrates a front sectional view of an irradiation device 100, in accordance with another embodiment of the present invention. Actuators in forms of a first electrical motor 352 and a second electrical motor 354 have been provided within the first end cap assembly 106 and the second end cap assembly 108, respectively. In that regard, the first 352 and the second 354 electrical motors may be synchronized motors that are capable of operating simultaneously to provide optimal torque and response times for motion of the movable lens 112. However, in several alternate embodiments, the first 352 and the second 354 electrical motors may serve different purposes. For example, the first electrical motor 352 may have the least measurable degree of rotation at least ten times that of the second electrical motor 354. In that regard, the first electrical motor 352 may be configured for coarse adjustment and the second electrical motor 354 may be configured for fine adjustment of the movable lens 112. Also, it is envisaged that, in several embodiments, the first 352 and the second 354 electrical motors may have self-locking shafts, such as worm and worm gear type or solenoid brake type arrangements, that prevent maladjustment of the movable lens 112 during utilization of the irradiation device 100. The self-locking shafts of the first 352 and the second 354 electrical motors may constitute the one or more locking arrangements for the embodiment of FIG. 3. Also, in construction, the first 352 and the second 354 electrical motors may be AC motors, DC motors, servo motors, stepper motors, or the like FIG. 4B illustrates a cross-sectional view of the irradiation device 100 of FIG. 4A, along a plane C-C. As illustrated in FIG. 4B, a segment 430 of the longitudinal shell 104 has been embodied as the fixed lens. The movable lens 112 is adapted to move linearly between the radiation source 110 and the segment 430. In that regard, lateral ends 402 and 404 of the movable lens 112 are adapted to slide along slots provided in constraint members 410 and 420, respectively, provided within the longitudinal shell 104, to prevent the motion of the movable lens 112 in lateral directions. The movable lens 112 and the segment 430 may be of any one or more types including concave, convex, or Fresnel lenses. However, the invention is not limited to the aforementioned concave, convex, and Fresnel lenses, instead, different types of lenses having distinct focal lengths can be used for the invention.

Figure 4C:
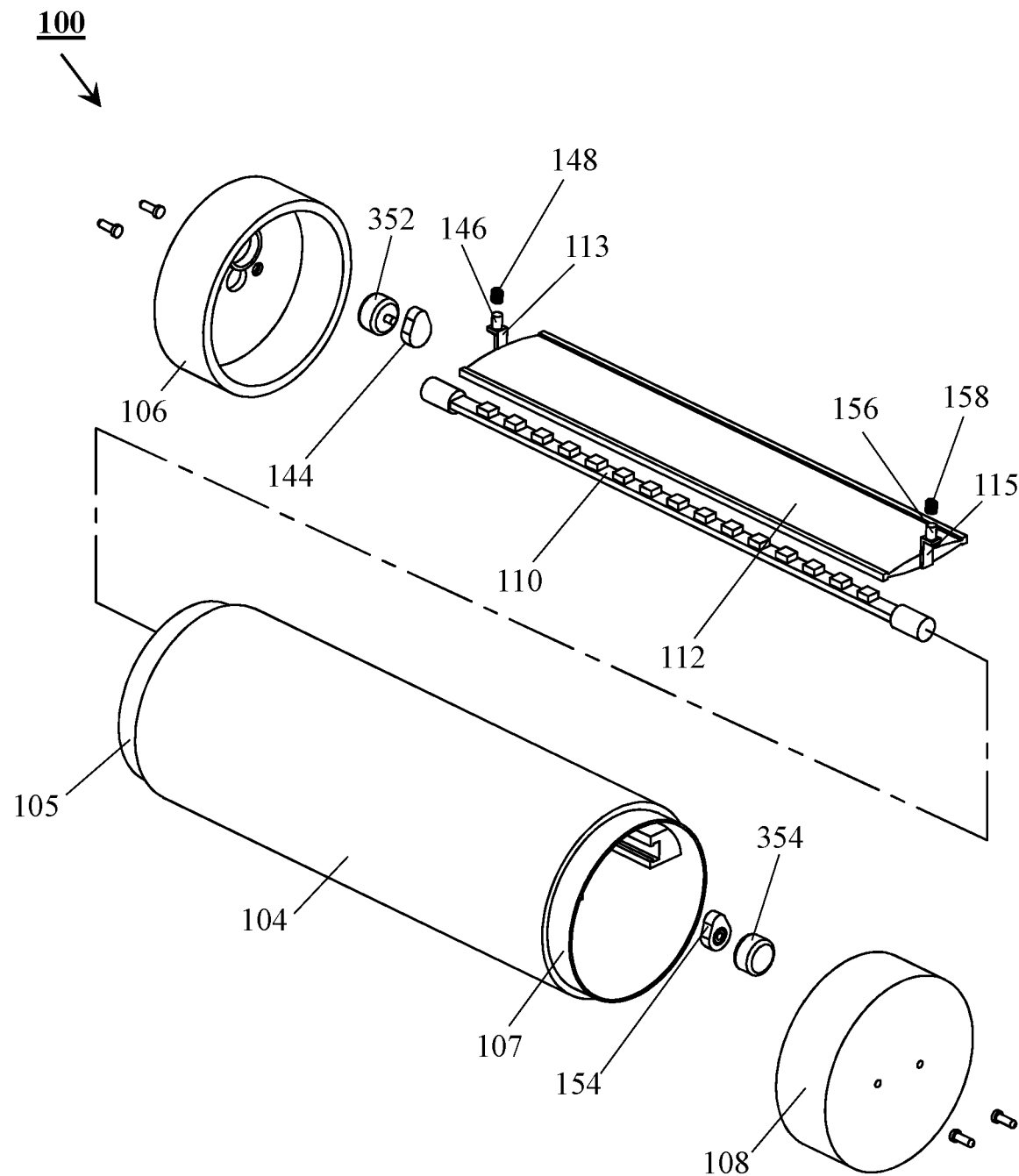
FIG. 4C illustrates an exploded view of the irradiation device of FIG. 4A.

FIG. 4C illustrates an exploded view of the irradiation device 100 of FIG. 4A. It can be observed from FIG. 4C, that the first translational mechanism 118 is constituted by the first cam 144 coupled with the first electrical motor 352, and the first cam follower 146 provided at the first end 113 of the movable lens 112. The first cam follower 146 is biased against the first cam 144 with the help of the first biasing spring element 148 that ensures that the first cam follower 146 always maintains contact with the first cam 144. Similarly, the second translational mechanism 120 is constituted by the second cam 154 coupled with the second electrical motor 354, and the second cam follower 156 provided at the second end 115 of the movable lens 112. The second cam follower 156 is biased against the second cam 154 with the help of the second biasing spring element 158 that ensures that the second cam follower 156 always maintains contact with the second cam 154. The discussion below elucidates the operation of the first translational mechanism 118, however, the same discussion, by extension, applies to the second translational mechanism 120 owing to their similar construction. It is also to be noted here that the invention does not necessitate the provision of actuators and translational mechanisms within both, the first 106 and the second 108 end cap assemblies, instead, same functionalities may be achieved with an actuator and a translational mechanism at any one of the first 106 and the second 108 end cap assemblies.

Figure 5A:
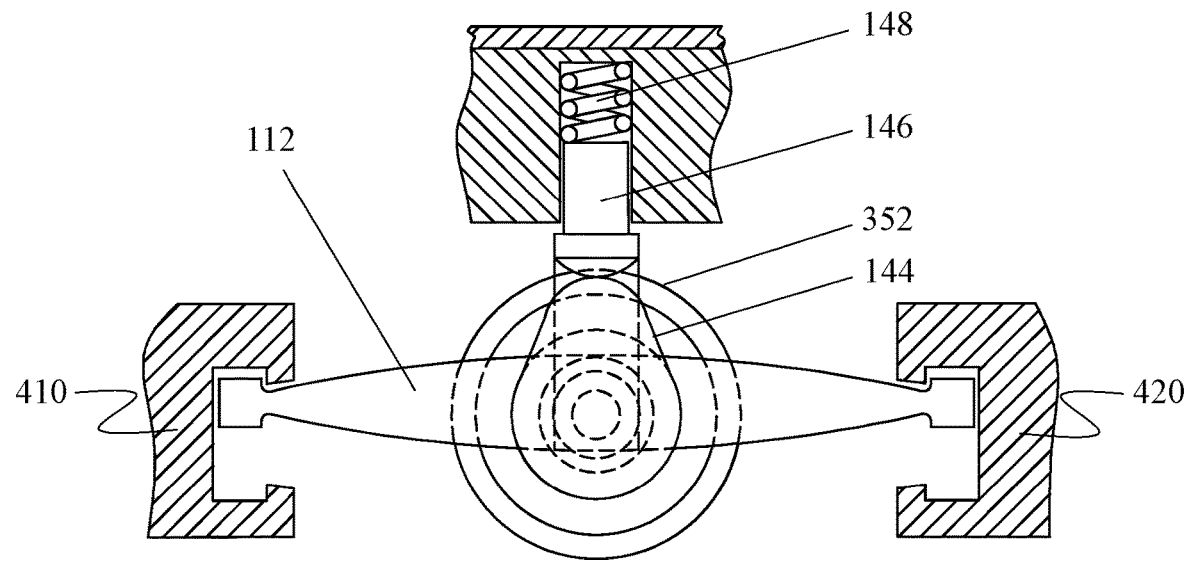
FIG. 5A illustrates a first position of a first translational mechanism of the irradiation device of FIG. 4A.

FIG. 5A illustrates a first position of the first translational mechanism 118 of the irradiation device 100 of FIG. 4A. The first position illustrated in FIG. 5A is indicative of the maximum displacement of the movable lens 112 from the radiation source 110. Here, the first cam follower 146 is at its highest position being in contact with the most eccentric segment of the first cam 144. Also, the first biasing spring element 148 is in a maximum compression state. The first biasing spring element 148 ensures that the first cam follower 146 is always in contact with the first cam 144 and the self-locking shaft of the first electrical motor 352 ensures that the first cam 144 does not rotate until an electrical current is supplied to the first electrical motor 352.

Figure 5B:
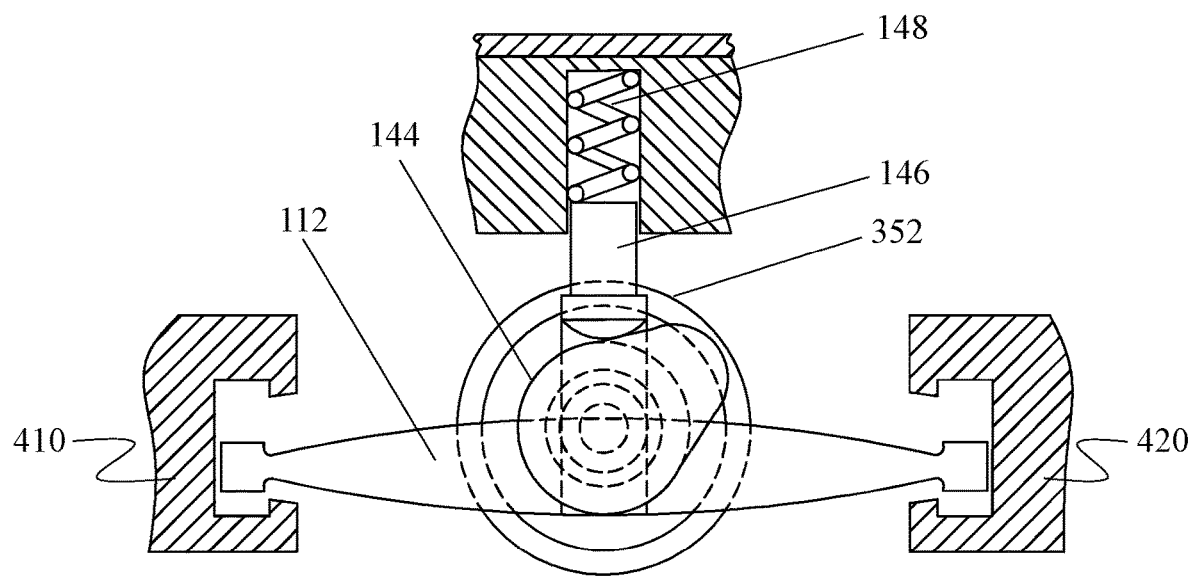
FIG. 5B illustrates a second position of the first translational mechanism of the irradiation device of FIG. 4A.

FIG. 5B illustrates a second position of the first translational mechanism 118 of the irradiation device 100 of FIG. 4A. The second position of FIG. 5B is indicative of the minimum displacement of the movable lens 112 from the radiation source 110. Here, the first cam follower 146 is at its lowest position being in contact with the least eccentric segment of the first cam 144. Also, the first biasing spring element 148 is in a minimum compression state. The first biasing spring element 148 ensures that the first cam follower 146 is always in contact with the first cam 144 and the self-locking shaft of the first electrical motor 352 ensures that the first cam 144 does not rotate until an electrical current is supplied to the first electrical motor 352. In either of the first and the second positions or any position in between, the constraint members 410 and 420 prevent lateral displacement of the movable lens 112.

In principle, the beam angle achieved is inversely proportional to a distance between the fixed lens (the segment 430 in this case) and the movable lens 112. For example, when the movable lens 112 is moved to the position near the radiation source 110, then the irradiation device 100 emits light at wide-angle (flood beam) and when it moves away from radiation source 110, the irradiation device 100 emits light at a narrow-angle (spot beam).

Figure 6A:
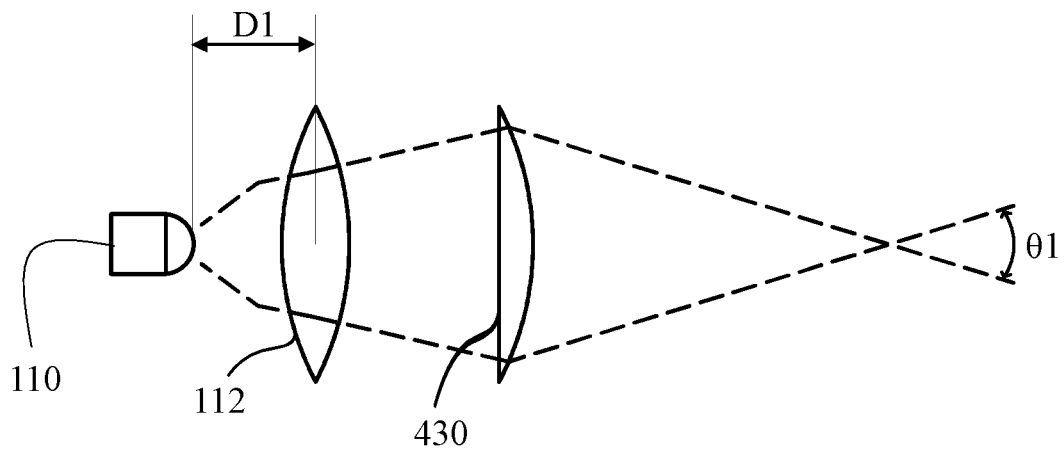
FIG. 6A illustrates a narrow beam emitted by the irradiation device, in accordance with an embodiment of the present invention.

FIG. 6A illustrates a narrow beam emitted by the irradiation device 100, in accordance with an embodiment of the present invention. The movable lens 112, and the segment 430 shown in FIG. 6A, are aligned with the radiation source 110, where D1 is the distance between the radiation source 110 and the movable lens 112, and ($\theta_1$) is the beam angle produced by the irradiation device 100.

Figure 6B:
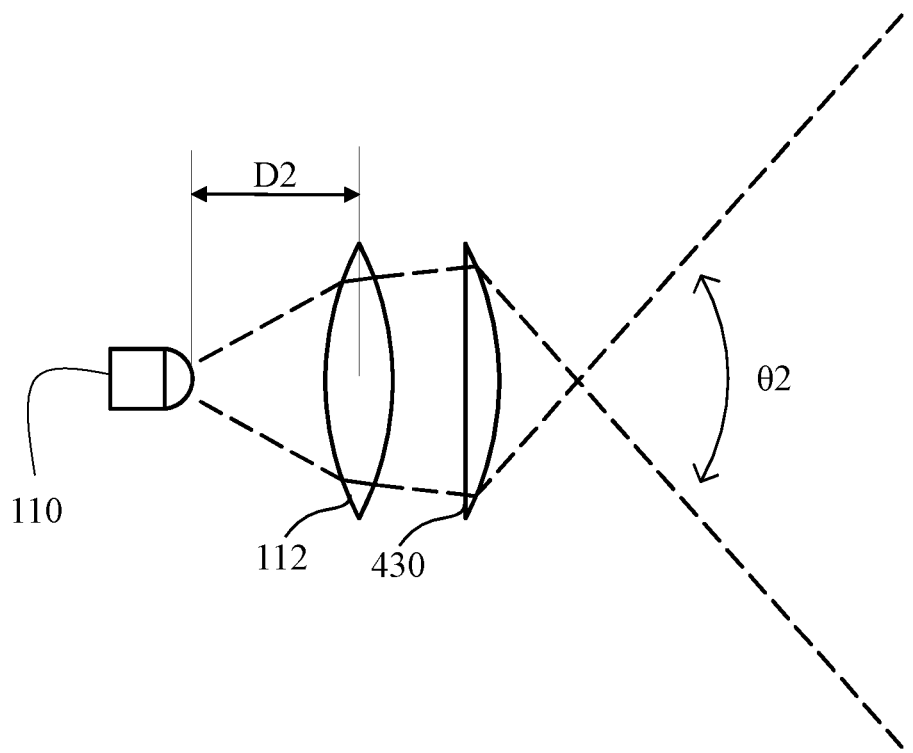
FIG. 6B illustrates a flood beam emitted by the irradiation device, in accordance with an embodiment of the present invention.

FIG. 6B illustrates a flood beam emitted by the irradiation device 100, in accordance with an embodiment of the present invention. The movable lens 112, and the segment 430 shown in FIG. 6B, are aligned with the radiation source 110, where D2 is the distance between the radiation source 110 and the movable lens 112, and ($\theta_2$) is the beam angle produced by the irradiation device 100. In this case, distance D2 is greater than the D1, and therefore the beam angle ($\theta_2$) is greater than the ($\theta_1$).

In use, a user may either manually rotate the one or more of the first 106 and the second 108 end cap assemblies or actuate the one or more of the first electrical motor 352 and the second electrical motor 354, of the irradiation device 100, either remotely or through a contact-based switch. Due to the rotational movement of one or more of the first cam 144 and the second cam 154, the movable lens 112 would displace linearly with respect to the radiation source 110 and the longitudinal shell 104.

It is further envisaged, that during the linear motion of the movable lens 112, special provisions may be made available to ensure that the radiation source 110 is inactive during the adjustment of the beam angle and other optical characteristics, to ensure power savings and undesirable light glare problems or exposure to undesirable radiations caused to an operator. For example, motion sensors may be installed on movable lens 112 and in the first 118 and the second 120 translational mechanisms, which may detect the motion of the movable lens 112 or the operation of the first 118 and the second 120 translational mechanisms and cause the deactivation of the radiation source 110. The deactivation of the radiation source 110 may also be facilitated through an electromechanical or solid-state switch that may be operated either automatically based on motion sensor feedback or manually by the operator.

The irradiation device 100 has been designed to operate both as a therapeutic device for non-invasive radiation treatment for conditions such as skin acne and aging, muscle spasms and inflammations and in some cases benign or malignant lesions and as an artificial lighting device in spatial lighting applications. In that regard, during utilization of the irradiation device 100 for therapeutic applications, the key factors that may affect the efficacy of the treatment include wavelengths, the power density of irradiation, time of exposure, distance of the affected area from the irradiation device 100 and mode of operation of the radiation source 110. In that regard, the radiation source 110 may be configured to operate in pulsed or continuous mode. As a further discussion, for input current of (I mA) and an applied voltage of (V Volts), the Input Power ($P_I$) being supplied to the irradiation device 100 would be given by equation (1).

$$P_I = V \times I \text{ mW} \tag{1}$$

For the overall efficiency ($\eta$) of the irradiation device 100, the Output Power ($P_O$) would be given by equation (2).

$$P_O = \eta \times P_I \text{ mW} \tag{2}$$

The area (A) being effectively irradiated by the irradiation device 100, with a beam angle ($\theta$), for a subject standing at a distance (d cm) would be given by equation (3).

$$A = \pi \times \left(d \times \tan\left(\frac{\theta}{2}\right)\right)^2 \text{ cm}^2 \tag{3}$$

Hence, the Power Density ($P_d$) being received at the distance (d) would be given by the equation (4).

$$P_d = K \times \frac{P_o}{A} \text{ mW/cm}^2 \tag{4}$$

Where K is the correction factor for accounting for the entire beam spread that will be greater than the beam angle. The correction factor 'K' may be empirically determined during the calibration of the irradiation device 100. Therefore, the dosage (D) and total irradiant energy ($E_a$) being absorbed by the subject, receiving treatment for a time period (T seconds) would be given by equations (5) and (6), respectively.

$$D = P_d \times T \text{ mJ/cm}^2 \tag{5}$$

$$E_a = D \times A \text{ mJ} \tag{6}$$

From equations (1) to (6) it can thus be inferred that for a given design of the irradiation device 100, the treatment received by the subject individual may be varied by varying parameters such as the input current, applied voltage, beam angle of the irradiation, distance of the subject from the irradiation device and treatment time, etc. For example, an effective dose for wound healing is 90 J/cm$^2$. It has to be further noted that the value of input current, applied voltage, and construction of the radiation source 110 (for example be it lasers or LEDs) will also be dictated by other factors such as type of condition (for example, acne, deep wounds, and lesions, etc.) and type of radiation output (for example, blue light, UV radiation, red light or IR radiation) suited for that condition.

Alternately, during utilization of the irradiation device 100 as an artificial lighting device for spatial lighting, a different set of characteristics come into play. Moreover, it is to be noted that in such applications the irradiation device 100 would most likely be emitting radiation in form of the wide spectrum visible light and therefore the efficacy of the irradiation device 100 would be evaluated differently than as described through equations (1) to (6). The key characteristics in the application of the irradiation device 100 for spatial lighting applications include angular span, beam angle, apex angle, and a distance of a surface being illuminated from the irradiation device 100, luminous intensity and luminous flux being emitted. For a surface at a distance (d) cm from the irradiation device 100, emitting visible light at a beam angle ($\theta$), the apex angle ($\alpha$) would be determined from equation (7) and angular span ($\sigma$) would be determined from equation (8).

$$\alpha = 2\theta \quad (7)$$

$$\sigma = 2\pi\left(1 - \cos\left(\frac{\alpha}{2}\right)\right) \text{ steradians} \quad (8)$$

For a given luminous intensity (C candela), the luminous flux (L) would be determined from equation (9).

$$L = C \times \sigma \text{ lumens} \quad (9)$$

Thus, the illumination of the surface, also known as the lux value at the surface may be determined by dividing the luminous flux (L) with the area (A) determined from equation (3). The lux value (l) is thus given by equation (10).

$$l = \frac{L}{A} \text{ lumens/cm}^2 \quad (10)$$

The lux value (l) is generally the value that is measured by light meters. Also, it can be seen from equation (10) and (3) that the lux value, therefore, depends on the beam angle and the distance of the surface from the irradiation device 100.

Figure 7:
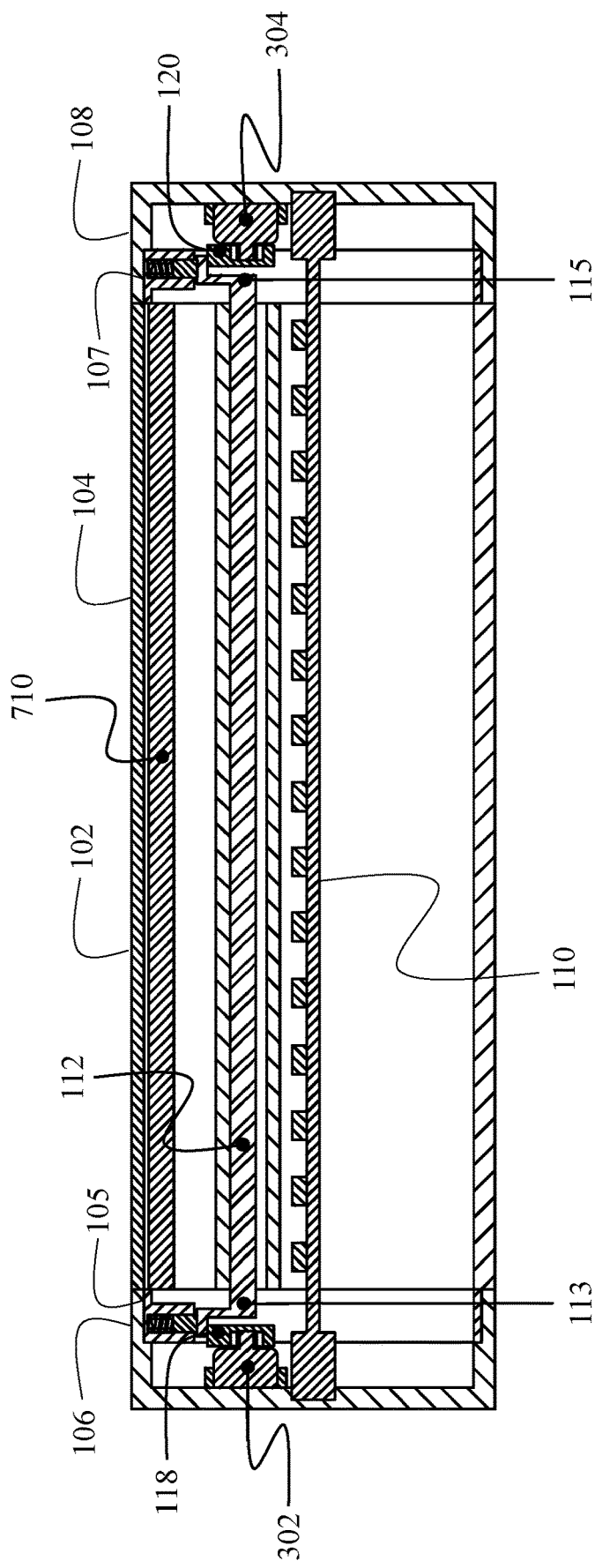
FIG. 7 illustrates a cross-sectional view of the irradiation device, in accordance with yet another embodiment of the present invention.

FIG. 7 illustrates a cross-sectional view of the irradiation device 100, in accordance with yet another embodiment of the present invention. In this embodiment, there is shown the fixed lens as a discrete member 710 provided within the longitudinal shell 104, both ends of the discrete member 710 being fixed to the inner lateral surfaces of the longitudinal shell 104. The main object of using the discrete member 710 as the fixed lens is to get a more focused and precise beam of light from irradiation device 100. Also, in certain modular designs, the discrete member 710 may be replaced with another discrete member for changing the output characteristics of the irradiation device 100 without a major device overhaul or purchase of a new device. In this embodiment, a movable lens 112 is also shown located between the discrete member 710 and the radiation source 110.

Example 1

As an example, for an irradiation device 100 rated at luminous intensity (C) of 1500 candela at an apex angle ($\alpha$) of 100 degrees, the beam angle ($\theta$), angular span ($\sigma$) and luminous flux (L) would be determined as below:

$$\theta = \frac{70}{2} = 50°$$

$$\sigma = 2\pi\left(1 - \cos\left(\frac{100}{2}\right)\right) = 2.244 \text{ steradians}$$

$$L = 2.244 \times 1500 = 3367 \text{ lumens}$$

For a surface that is at a distance of 1 m or 100 cm from the irradiation device 100, the illumination of the surface or lux value (l) would be determined as follows:

$$A = \pi \times \left(100 \times \tan\frac{35}{2}\right)^2 = 3123.2 \text{ cm}^2$$

$$l = \frac{3367}{3123.2} = 1.078 \text{ lumens/cm}^2$$

The embodiments of the invention as described above offer several advantages including simplicity in design and construction, novel and inventive use of readily available materials. Further, the incorporation of LEDs as the radiation source provides significant power economies. Also, the use of cams for beam angle adjustment allows potentially infinite values of beam angles to be achieved within a designed range. The same construction of the irradiation device can be used for multiple applications with minor constructional modifications. The modular nature of the fixed lens as described in the second embodiment allows for a high level of flexibility in achieving desired characteristics of the output radiation with minimal redesign and adjustment. Moreover, the operation of the device does not demand special skills on the part of the user or the operator and is therefore suited for both domestic applications (where convenience is the key) and commercial applications (where the economy is the key).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An irradiation device capable of emitting electromagnetic radiation at variable beam angles, the irradiation device comprising:
 a housing assembly including:
 a longitudinal shell, the longitudinal shell having a first end and a second end,
 a first end cap assembly provided at the first end of the longitudinal shell,
 a second end cap assembly provided at the second end of the longitudinal shell, and one or more locking arrangements provided at one or more of the first and the second ends of the longitudinal shell, the one or more locking arrangements being adapted to prevent linear motion and/or accidental rotational motion of the one of first and the second end cap assemblies with respect to the one or more of the first and the second ends of the longitudinal shell, respectively;

a radiation source provided within the longitudinal shell, wherein the radiation source is configured to emit electromagnetic radiation, and the longitudinal shell is made from a material that is at least partially transparent to the electromagnetic radiation emitted by the radiation source;

a movable lens having two ends, a first end of the movable lens provided within the first end cap assembly and a second end of the movable lens provided within the second end cap assembly, wherein the movable lens is located between the radiation source and the longitudinal shell;

one or more translational mechanisms provided within one or more of the first end cap assembly and the second end cap assembly, wherein the one or more translational mechanisms are adapted to cause a linear motion of the movable lens with respect to the radiation source, one or more electrical motors provided within one or both of the first end cap assembly and the second end cap assembly, wherein the one or more electrical motors are configured to cause actuation of the respective one or more translational mechanisms;

wherein each one of the one or more locking arrangements is constituted by one or more self-locking shafts provided with the one or more respective electrical motors.

2. The irradiation device as claimed in claim 1, wherein at least a segment of the longitudinal shell is embodied as a fixed lens.

3. The irradiation device as claimed in claim 1, further comprising a fixed lens in the form of a discrete member located between the radiation source and the longitudinal shell.

4. The irradiation device as claimed in claim 1, wherein the radiation source is configured to be deactivated during the linear motion of the movable lens.

5. The irradiation device as claimed in claim 1, wherein the one or more of the first and the second end cap assemblies are adapted to be rotated manually with respect to the longitudinal shell, thereby causing actuation of the respective one or more translational mechanisms.

6. The irradiation device as claimed in claim 1, wherein each one of the one or more the translation mechanisms is constituted by a cam that is adapted to rotate on actuation of the respective translational mechanism and a cam follower provided at an end of the movable lens.

7. The irradiation device as claimed in claim 1, wherein the radiation source is configured to emit the electromagnetic radiation in ultra-violet (UV), visible light and infrared (IR) wavelengths bands of the electromagnetic spectrum.

8. The irradiation device as claimed in claim 1, wherein the radiation source is configured to emit the electromagnetic radiation in any one of a pulse mode and continuous mode.

9. The irradiation device as claimed in claim 1, wherein the radiation source includes one or more light emitting diodes (LEDs).

10. The irradiation device as claimed in claim 9, wherein the one or more LEDs are provided on an organic LED (OLED) based flexible panel or an inorganic LED based flexible panel.

11. The irradiation device as claimed in claim 9, wherein the one or more LEDs are provided as a printable composition of micro-LEDs, printed on a substrate.

\* \* \* \* \*